United States Patent [19]
Frey et al.

[11] Patent Number: 5,442,412
[45] Date of Patent: Aug. 15, 1995

[54] PATIENT RESPONSIVE EYE FIXATION TARGET METHOD AND SYSTEM

[75] Inventors: Rudolph W. Frey; George R. Downes, Jr., both of Orlando, Fla.

[73] Assignee: Autonomous Technologies Corp., Orlando, Fla.

[21] Appl. No.: 232,959

[22] Filed: Apr. 25, 1994

[51] Int. Cl.$^6$ ............................................. A61B 3/02
[52] U.S. Cl. .................................. 351/223; 351/208; 351/243
[58] Field of Search ............... 351/208, 205, 223, 222, 351/237, 243, 211; 356/3, 138, 150

[56] References Cited

U.S. PATENT DOCUMENTS 3,600,098  8/1971  Mohrman ........................... 351/208

FOREIGN PATENT DOCUMENTS 6-114006  4/1994  Japan ................................. 351/208

*Primary Examiner*—William L. Sikes
*Assistant Examiner*—Huy Mai

[57] ABSTRACT

A biofeedback method and system provide eye position feedback to a patient. A first light source produces a ring of visible light centered about an optical axis at a perceived first position. A second light source produces a dot of visible light centered on the same optical axis as that of the ring at a perceived second position. As perceived by the eye, the ring's first position is closer to the eye than the dot's second position. The eye will further perceive the dot as being centered in the ring when the eye moves its visual axis into spatial and angular alignment with the optical axis shared by the dot and ring. An eye movement sensor detects a quantifiable amount of eye movement to generate an error signal. The error signal is supplied to the second light source to adjust the dot's appearance whenever the patient needs to realign the eye's visual axis with the optical axis of the dot and the ring. The invention may also include a third light source to produce a directing light at a visually resolvable angle from the dot in a direction that is approximately opposite to the direction of eye movement.

23 Claims, 4 Drawing Sheets

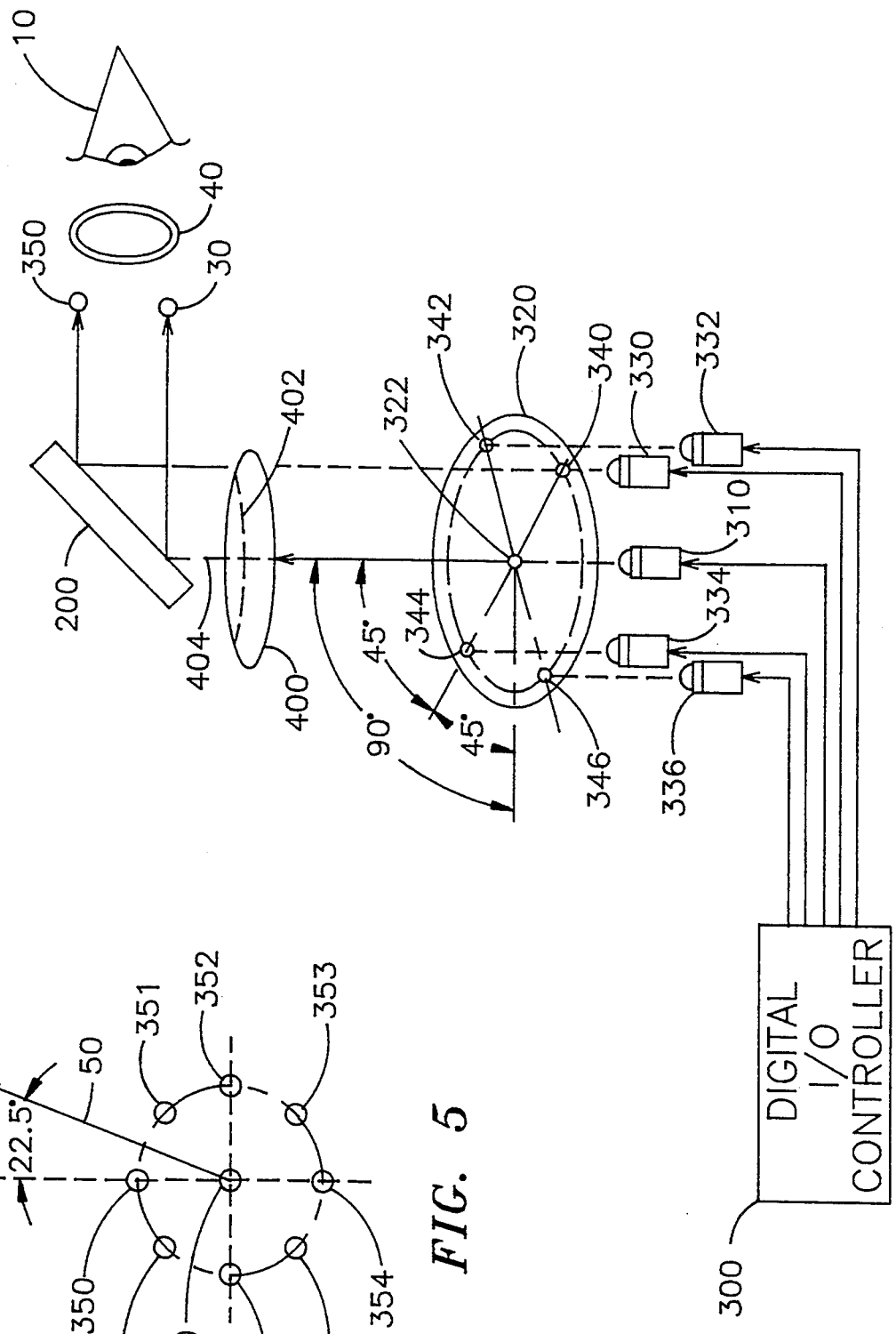

PATIENT RESPONSIVE EYE FIXATION TARGET METHOD AND SYSTEM

This patent application is copending with related patent application entitled "Eye Movement Sensing Method and System" filed on the same date and owned by the common assignee as subject patent application. The disclosure of that application is incorporated herein by reference.

FIELD OF THE INVENTION

The invention relates generally to biofeedback mechanisms, and more particularly to a patient responsive eye fixation target that provides a patient with biofeedback on the patient's eye position.

BACKGROUND OF THE INVENTION

A variety of ophthalmic procedures, ranging from retinal examinations to a variety of laser surgery procedures, require or may be enhanced by some methodology/apparatus for fixing the position of the eye. One approach uses a grasping device or suction ring to physically hold the patient's eye stable. However, the intrusive nature of the suction ring may distort the eye's shape thereby affecting examination and/or surgical precision. Further, since the suction ring is held by the ophthalmic practitioner, the practitioner's low frequency but large amplitude hand motions become a factor in procedural precision.

SUMMARY OF THE INVENTION

Accordingly, it is an object of the present invention to provide a patient with biofeedback on the patient's eye position.

Another object of the present invention is to provide a non-intrusive method and system that supplies a patient with biofeedback on the patient's eye position.

Still another object of the present invention is to provide a method and system that supplies a patient with biofeedback by providing the patient with: 1) an indication that eye movement from a predetermined position has occurred, 2) a response required to change the eye position back to the predetermined position, and 3) an indication that the predetermined position has again been attained.

Other objects and advantages of the present invention will become more obvious hereinafter in the specification and drawings.

In accordance with the present invention, a biofeedback mechanism provides eye position feedback to a patient. A first light source produces a ring of visible light centered about an optical axis. The ring is perceivable by an eye of the patient at a first position. A second light source produces a dot of visible light centered on the same optical axis as that of the ring. The dot is perceivable by the eye of the patient at a second position. The ring's first position is perceived by the eye as being closer to the eye than the dot's second position. The eye will further perceive the dot as being centered in the ring when the patient moves the eye to bring its visual axis into alignment with the optical axis shared by the dot and ring. An eye movement sensor detects a quantifiable amount of eye movement and generates an eye movement error signal based on the eye movement. The eye movement error signal is supplied to the second light source to adjust the dot's appearance whenever the patient needs to realign the eye's visual axis with the optical axis of the dot and the ring. The invention may also include a third light source to produce a directing light at a visually resolvable angle from the dot in a direction that is approximately opposite to the direction of eye movement.

BRIEF DESCRIPTION OF THE DRAWINGS

FIG. 4 is a block diagram of a portion of the second embodiment patient responsive target system; and FIG. 5 is a diagrammatic representation of the projection positions of eight directional light dots positioned on a circle about the aligning light dot in accordance with a modification of the second embodiment of the present invention.

DETAILED DESCRIPTION OF THE INVENTION

Figure 1:
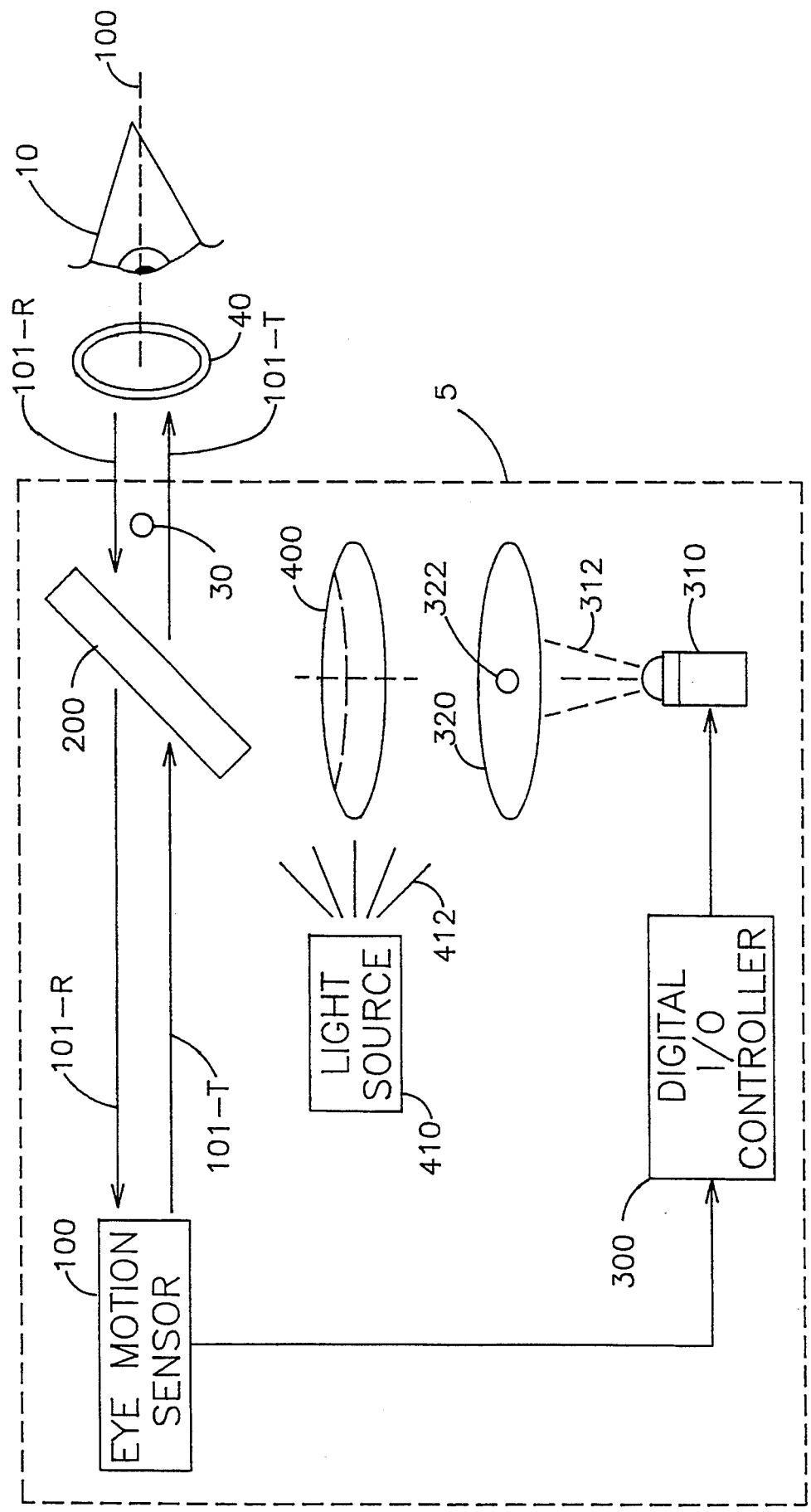
FIG. 1 is a block diagram of a system used for providing a patient with biofeedback on the patient's eye position in accordance with a first embodiment of the present invention.

Referring now to the drawings, and more particularly to FIG. 1, a block diagram of a first embodiment patient responsive eye fixation target system is shown and contained within the dotted line box designated by reference numeral 5. System 5 generates and adjusts a patient responsive eye fixation target to provide the patient with a measure of biofeedback concerning the patient's eye position. In this embodiment, the fixation target consists of a dot of light 30 and a ring of light 40. Dot 30 is projected by system 5 to appear to eye 10 as if it is far away, i.e., at infinity. Ring 40 is projected by system 5 to appear to eye 10 as if it is close to eye 10 relative to dot 30, e.g., typically at a distance in the range of approximately 15–20 inches. (As will be explained further below, this is accomplished by placing lens 400 8–12 inches from eye 10.)

System 5 projects dot 30 and ring 40 such that they are both centered on and about, respectively, a common optical axis represented by dotted line 500. When the patient aligns visual axis 10a of eye 10 with optical axis 500 such that visual axis 10a and optical axis 500 are angularly and spatially aligned (e.g., collinear, parallel, etc.), dot 30 is perceived by eye 10 as if it is centered in ring 40. Since dot 30 appears at infinity, axis 10a must be parallel to optical axis 500 to focus on it. In this way, ring 40 becomes a spatial reference and dot 30 becomes an angular reference for eye 10. Ring 40 must appear closer to eye 10 than dot 30 so that as the patient's visual axis 10a translates, the position of dot 30 appears to move with respect to ring 40. The farther away dot 30 appears, the more accurate the angular alignment will be.

When eye 10 strays from its alignment with respect to dot 30 and ring 40, either voluntarily or involuntarily, system 5 detects such movement and uses same to alter the appearance of dot 30 as a means of alerting the patient that he is no longer aligned with dot 30 and ring 40. Altering the appearance of dot 30 can be implemented in a variety of fashions without departing from the scope of the present invention. For example, dot 30 could be made to flash "on" and "off" or change color when eye 10 strays from its focus. To summarize, system 5 can be functionally divided into the detecting of eye movement, the production of ring 40, and the production of dot 30 as well as its alteration based on eye movement.

With respect to the detection of eye movement, eye movement sensor 100 transmits light energy 101-T towards eye 10 and receives reflected light energy 101-R from the surface of eye 10. Reflected light energy 101-R is used to determine eye movement. Optically disposed between eye movement sensor 100 and eye 10 is dichroic beamsplitter 200. Beamsplitter 200 is selected to transmit wavelengths of light associated with light energies 101-T/101-R while reflecting wavelengths of light generated by that portion of system 5 associated with the production of dot 30 and ring 40. In this way, all of system 5 can be referenced to the same optical axis.

In order to take advantage of the transmission/reflection properties of beamsplitter 200, light energy 101-T (and 101-R) must be of a different wavelength than that of dot 30 and ring 40. Further, in view of the fact that the present invention is to be used in ophthalmic procedures, the safety of light energy 101-T must be taken into consideration. In particular, the light energy must be "eye safe" to meet the American National Standards Institute (ANSI) safety requirements. The light energy should also preferably lie outside the visible spectrum so as not to interfere or obstruct a doctor's view of the eye undergoing the ophthalmic procedure. While a variety of light wavelengths satisfy the above requirements, by way of example, light energy 101-T is infrared light energy in the 900 nanometer wavelength region. Light in this region meets the above noted criteria and is further produced by readily available, economically affordable light sources. One such light source is a high pulse repetition rate GaAs 905 nanometer laser operating at 4 kHz which produces an ANSI defined eye safe pulse of 10 nanojoules in a 50 nanosecond pulse.

Figure 2:
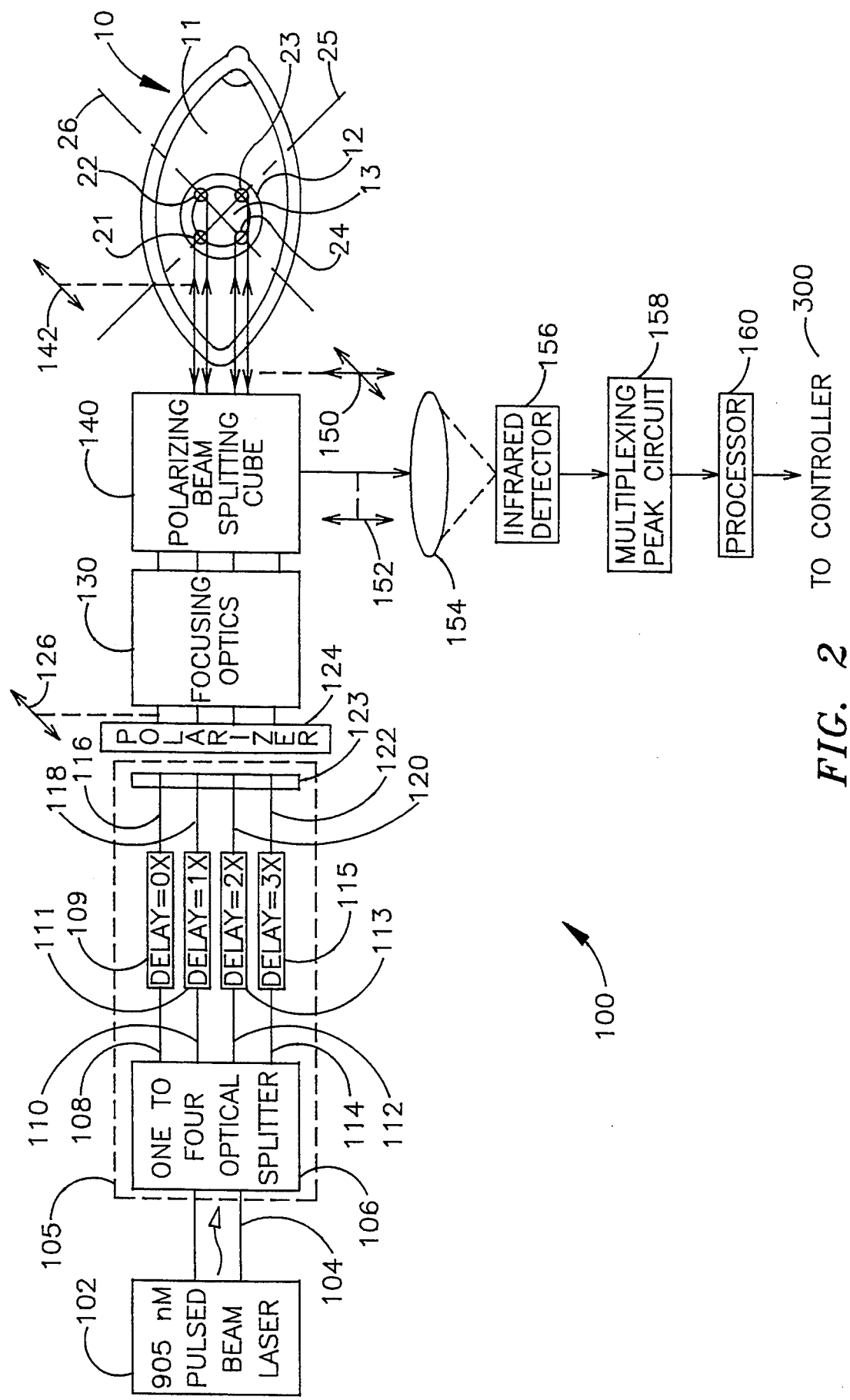
FIG. 2 is a block diagram of a preferred embodiment eye movement sensor.

A preferred embodiment method for determining the amount of eye movement, as well as eye movement sensor 100 for carrying out such a method, are described in detail in the aforementioned copending patent application. However, for purpose of a complete description, sensor 100 will be described briefly with the aid of the block diagram shown in FIG. 2. Sensor 100 may be broken down into a delivery portion and a receiving portion. Essentially, the delivery portion projects light energy 101-T in the form of light spots 21, 22, 23 and 24 onto a boundary (e.g., iris/pupil boundary 14) on the surface of eye 10. The receiving portion monitors light energy 101-R in the form of reflections caused by light spots 21, 22, 23 and 24.

In delivery, spots 21 and 23 are focused and positioned on axis 25 while spots 22 and 24 are focused and positioned on axis 26 as shown. Axes 25 and 26 are orthogonal to one another. Spots 21, 22, 23 and 24 are focused to be incident on and evenly spaced about iris/pupil boundary 14. The four spots 21, 22, 23 and 24 are of equal energy and are spaced evenly about and on iris/pupil boundary 14. This placement provides for two-axis motion sensing in the following manner. Each light spot 21, 22, 23 and 24 causes a certain amount of reflection at its position on iris/pupil boundary 14. Since boundary 14 moves in coincidence with eye movement, the amount of reflection from light spots 21, 22, 23 and 24 changes in accordance with eye movement. By spacing the four spots evenly about the circular boundary geometry, horizontal or vertical eye movement is detected by changes in the amount of reflection from adjacent pairs of spots. For example, horizontal eye movement is monitored by comparing the combined reflection from light spots 21 and 24 with the combined reflection from light spots 22 and 23. In a similar fashion, vertical eye movement is monitored by comparing the combined reflection from light spots 21 and 22 with the combined reflection from light spots 23 and 24.

More specifically, the delivery portion includes a 905 nanometer pulsed diode laser 102 transmitting light through optical fiber 104 to an optical fiber assembly 105 that splits and delays each pulse from laser 102 into preferably four equal energy pulses. Assembly 105 includes one-to-four optical splitter 106 that outputs four pulses of equal energy into optical fibers 108, 110, 112, 114. In order to use a single processor to process the reflections caused by each pulse transmitted by fibers 108, 110, 112 and 114, each pulse is uniquely delayed by a respective fiber optic delay line 109, 111, 113 and 115. For example, delay line 109 causes a delay of zero, i.e., DELAY=0x where x is the delay increment; delay line 111 causes a delay of x, i.e., DELAY=1x; etc.

The pulse repetition frequency and delay increment x are chosen so that the data rate of sensor 100 is greater than the speed of the movement of interest. In terms of saccadic eye movement, the data rate of sensor 100 must be on the order of at least several hundred hertz. For example, a sensor data rate of approximately 4 kHz is achieved by 1) selecting a small but sufficient value for x to allow processor 160 to handle the data (e.g., 160 nanoseconds), and 2) selecting the time between pulses from laser 102 to be 250 microseconds (i.e., laser 102 is pulsed at a 4 kHz rate).

The four equal energy pulses exit assembly 105 via optical fibers 116, 118, 120 and 122 which are configured as a fiber optic bundle 123. Bundle 123 arranges the optical fibers such that the center of each fiber forms the corner of a square. Light from assembly 105 is passed through an optical polarizer 124 that outputs horizontally polarized light beams as indicated by arrow 126. Horizontally polarized light beams 126 pass to focusing optics 130 where spacing between beams 126 is adjusted based on the boundary of interest. Additionally, a zoom capability (not shown) can be provided to allow for adjustment of the size of the pattern formed by spots 21, 22, 23 and 24. This capability allows sensor 100 to adapt to different patients, boundaries, etc.

A polarizing beam splitting cube 140 receives horizontally polarized light beams 126 from focusing optics 130. Cube 140 is configured to transmit horizontal polarization and reflect vertical polarization. Accordingly, cube 140 transmits only horizontally polarized light beams 126 as indicated by arrow 142. Thus, it is only horizontally polarized light that is incident on eye 10 as spots 21, 22, 23 and 24. Upon reflection from eye 10, the light energy is depolarized (i.e., it has both horizontal and vertical polarization components) as indicated by crossed arrows 150.

The receiving portion first directs the vertical component of the reflected light as indicated by arrow 152. Thus, cube 140 serves to separate the transmitted light energy from the reflected light energy for accurate measurement. The vertically polarized portion of the reflection from spots 21, 22, 23 and 24, is passed through focusing lens 154 for imaging onto an infrared detector 156. Detector 156 passes its signal to a multiplexing peak detecting circuit 158 which is essentially a plurality of peak sample and hold circuits, a variety of which are well known in the art. Circuit 158 is configured to sample (and hold the peak value from) detector 156 in accordance with the pulse repetition frequency of laser 102 and the delay x. For example, if the pulse repetition frequency of laser 102 is 4 kHz, circuit 158 gathers reflections from spots 21, 22, 23 and 24 every 250 microseconds.

The values associated with the reflected energy for each group of four spots (i.e., each pulse of laser 102) are passed to a processor 160 where horizontal and vertical components of eye movement are determined. For example let $R_{21}$, $R_{22}$, $R_{23}$ and $R_{24}$ represent the detected amount of reflection from one group of spots 21, 22, 23 and 24, respectively. A quantitative amount of horizontal movement is determined directly from the normalized relationship $$\frac{(R_{21} + R_{24}) - (R_{22} + R_{23})}{R_{21} + R_{22} + R_{23} + R_{24}} \quad (1)$$

while a quantitative amount of vertical movement is determined directly from the normalized relationship $$\frac{(R_{21} + R_{22}) - (R_{23} + R_{24})}{R_{21} + R_{22} + R_{23} + R_{24}} \quad (2)$$

Note that normalizing (i.e., dividing by $R_{21}+R_{22}+R_{23}+R_{24}$) reduces the effects of variations in signal strength. Once determined, the measured amounts of eye movement are sent to digital input/output (I/O) controller 300.

Figure 3A:
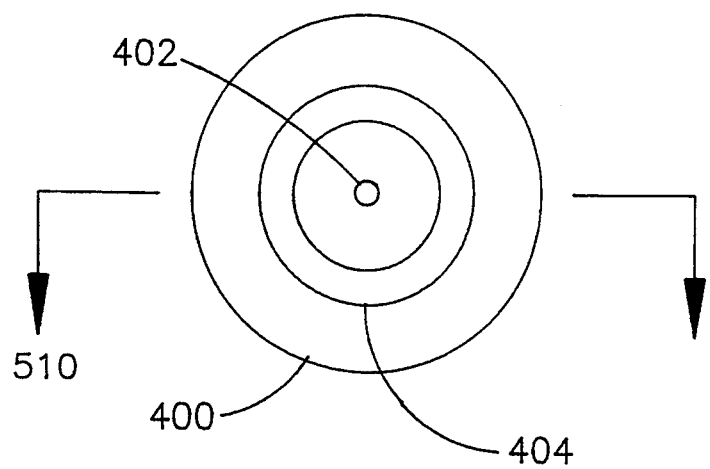
FIG. 3A is a plan view of the convex lens having a circular channel cut in one face thereof.
Figure 3B:
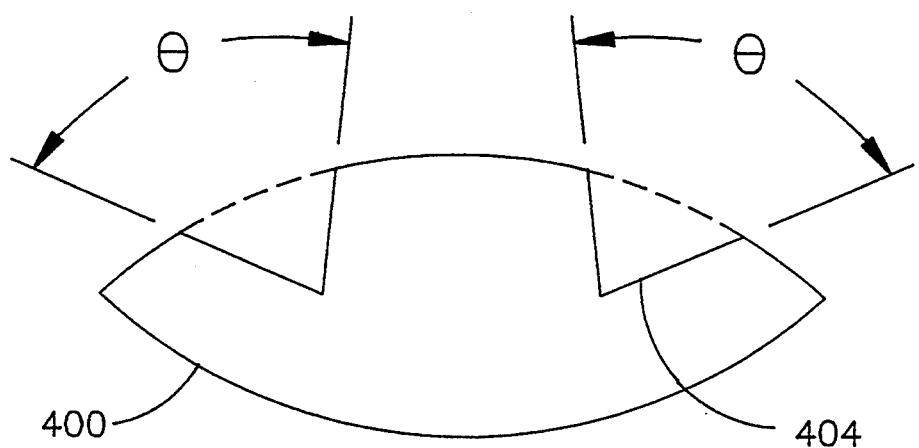
FIG. 3B is a cross-sectional view of the convex lens in FIG. 3A as taken along line 3—3.

With respect to the production of ring 40, convex lens 400, light source 410 and circular reticle 420 are provided. Convex lens 400 and reticle 420 have their optical axes aligned with optical axis 500. Circular reticle 420 is a clear plastic window having a circular channel of v-shaped cross-section scored in one face thereof as represented by dotted line 422. Channel 422 is shown in more detail in the plan view of FIG. 3A and cross-sectional view of FIG. 3B which has been taken along line 3—3 of FIG. 3A.

Ring 40 is produced by illuminating reticle 420 with visible light (e.g., white light) 412 from light source 410 located at the edge of reticle 420. More specifically, light source 410 illuminates reticle 420 with light 412 from a position that is approximately 90° with respect to optical axis 500. Channel 422 serves to reflect light 412 in all directions diffusely such that the (white) light from light source 410 is perceived by the patient's eye as ring 40 as eye 10 focuses through lens 400 along optical axis 500, i.e, focuses on dot 30. While a simple scratch in reticle 420 would produce this effect, channel 422 is cut to diffuse enough of light 412 so that ring 40 is bright enough for eye 10 to use as a reference.

Typically, a pointed tool would be used to create v-shaped channel 422 having an acute angle $\theta$. In this way, ring 40 appears as a sharp reference. The cut surface of channel 422 is sufficiently rough to diffusely reflect, i.e., reflect in all directions, light 412. By way of example, for a reticle that is typically 0.6 inches in diameter, the diameter of channel 422 varies between 0.04–0.06 inches when used with lens 400 having a focal length of 40 mm.

With respect to the production of dot 30 and alteration thereof based on eye movement, digital input/output (I/O) controller 300, light emitting diode (LED) 310, field stop 320, and convex lens 400 are provided. In terms of production of dot 30, LED 310 produces visible light 312 of at least one color incident on field stop 320. Pinhole 322 (e.g., on the order of 300 microns in diameter) of field stop 320 allows a portion of light 312 to pass through to convex lens 400 where it is collimated and reflects off beamsplitter 200 to appear as dot 30. In order to have dot 30 perceived by eye 10 as being far away, e.g., at infinity, filed stop 320/pinhole 322 is positioned at a distance from convex lens 400 equal to the focal length of convex lens 400.

In terms of the alteration of dot 30 based on eye movement, digital I/O controller 300 receives a signal from eye movement sensor 100 indicative of eye movement. I/O controller 300 converts the incoming signal to a voltage that drives LED 310. For example, if LED 310 is a single color LED, controller 300 issues 1) a steady supply voltage to LED 310 when there is no eye movement, and 2) a sequence of "on"/"off" supply voltages to LED 310 when eye movement is detected by eye movement sensor 100 or vice versa. In this way, LED 310 would flash to alert the patient that his eye 10 has strayed from focusing on dot 30. Alternatively, LED 310 could be a two-color LED that produces one of the two colors dependent on the supply voltage. In this case, controller 300 issues 1) a first supply voltage to LED 310 to cause LED 310 to produce light of a first color when there is no eye movement, and 2) a second supply voltage to LED 310 to cause LED 310 to produce light of a second color when there is eye movement. Digital I/O plug-in boards for personal computers are controllers capable of functioning in this manner and are well known in the art. One such controller is model IL5C-40/80-P-10-V manufactured by National Instruments.

The eye movement feedback provided by the present invention can be further enhanced. In particular, a second embodiment of the present invention provides the patient with not only the indication of eye movement, but also the direction that eye 10 must move to get back to its focus on dot 30. To do this, a plurality of directional LEDs 330, 332, 334, and 336 are positioned equidistantly on a circle about LED 310 as shown in FIG. 4. For sake of clarity, only the additional elements/features of this second embodiment are shown in FIG. 4. The remainder of the fixation target system remains and operates as described above.

In FIG. 4, directional LEDs 330, 332, 334 and 336 are positioned behind corresponding pinholes 340, 342, 344 and 346. Typically, each of pinholes 341, 342, 344 and 346 is sized in accordance with that of pinhole 322. Since the preferred embodiment eye movement sensor 100 is capable of detecting the direction of eye movement, controller 300 can use such direction to light one of directional LEDs 330, 332, 334 and 336 that is closest to being 180° away from the direction of eye movement.

For example, if eye movement were in a direction that was in line with LED 334/pinhole 344, LED 330 would be lit to produce a directional light dot 350 at a visually resolvable angle from dot 30. For the four directional LED configuration shown, LED 330 would be lit for eye movement occurring anywhere in the 90° angular window centered on pinhole 344 as shown. Thus, for the four LED configuration, a directional light dot will always appear to eye 10 from a position that is between 135°–225° away from the direction of eye movement.

To increase the precision of the directional feedback, additional directional LED's can be added. For example, if eight directional LEDs were equidistantly positioned on a circle around LED 310, a directional light dot will always appear to eye 10 from a position that is between 157.5°–225° away from the direction of eye movement. This is shown diagrammatically in FIG. 5 where projection positions of eight directional light dots 350–357 are positioned on a circle about dot 30. If eye movement were along a direction indicated by arrow 50 that is exactly between dots 350 and 351, either of dots 354 or 355 could be lit to alert the patient to move the eye's focus opposite to direction 50 and towards dot 30. The number of additional directional LEDs should strike a balance with what is distinguishable by the patient's eye. However, at a minimum, the above described four directional LED configuration should be used.

The patient's eye will perceive the particular directional light dot at infinity. The directional LEDs and corresponding pinholes in attenuator 320 are configured to preferably project the directional light dots within ring 40. However, the directional light dots can also be projected outside of ring 40 depending on their color, size, etc.

Eye movement generated alteration of light dot 30 and production of a corresponding directional light dot are both governed by I/O controller 300. For example, eye movement can be used to turn off dot 30, turn "on" or flash "on"/"off" a directional light dot until such time that eye 10 has realigned visual axis 10*a* with dot 30. Alternatively, eye movement could trigger a flashing "on"/"off" sequence of dot 30 and lighting of a different color directional light dot. Accordingly, it is to be understood that the particular type of lighting color and/or sequencing is not a limitation of the present invention. As with the first embodiment, controller 300 can be implemented with the above identified National Instruments controller since the above-identified model provides 96 outputs.

The advantages of the present invention are numerous. A non-intrusive biofeedback method and system are provided to alert a patient that unwanted eye movement is causing the patient's eye to stray from a desired position. The method and system also indicate when the patient's eye has returned to the desired position. Finally, the method and system are easily enhanced to provide the patient with directional information regarding how the patient should move his eye to return to the desired position. The present invention will find utility in a wide variety of ophthalmic procedures ranging from simple exams to complex laser surgery procedures.

Although the invention has been described relative to a specific embodiment thereof, there are numerous variations and modifications that will be readily apparent to those skilled in the art in the light of the above teachings. It is therefore to be understood that, within the scope of the appended claims, the invention may be practiced other than as specifically described.

What is claimed and desired to be secured by Letters Patent of the United States is:

1. A biofeedback mechanism for providing eye position feedback to a patient, comprising:

a first light source for producing a ring of visible light centered about an optical axis and perceivable by an eye of said patient at a first position, said eye having a visual axis;

a second light source for producing a dot of visible light centered on said optical axis and perceivable by said eye of said patient at a second position, wherein said first position is perceived by said eye as being closer to said eye than said second position, and wherein said eye perceives said dot as being centered in said ring when said eye moves said visual axis into spatial and angular alignment with said optical axis; and an eye movement sensor operatively connected to said second light source for detecting a quantifiable amount of movement of said eye and for generating an eye movement error signal based on said quantifiable amount, said eye movement error signal being supplied to said second light source, wherein said second light source adjusts said dot's appearance based on said eye movement error signal to indicate to said patient to realign said visual axis with said optical axis of said dot and said ring.

2. A biofeedback mechanism as in claim 1 wherein said first light source comprises:

a reticle having a circular channel cut in one face thereof, said circular channel centered on said optical axis and lying in a plane that is orthogonal to said optical axis; and a light for illuminating said reticle from a position approximately 90° to said optical axis.

3. A biofeedback mechanism as in claim 2 wherein said circular channel has a v-shaped cross-section.

4. A biofeedback mechanism as in claim 2 wherein said light is white light.

5. A biofeedback mechanism as in claim 2 wherein said second light source comprises:

a light emitting diode (LED) for producing visible light;

a field stop having a pinhole positioned in front of said LED for passing only a portion of said visible light as said dot, said field stop further being positioned between said LED and a lens at a distance from said lens that is equivalent to said lens' focal length; and a controller responsive to said eye movement error signal for controlling the production of said visible light by said LED.

6. A biofeedback mechanism as in claim 5 wherein said eye movement error signal includes angular orientation of said quantifiable amount of movement of said eye, said biofeedback mechanism further comprising:

a third light source consisting of a plurality of LEDs arranged in a circle centered about said LED producing said visible light used for producing said dot; and said field stop being positioned in front of said plurality of LEDs arranged in said circle, said field stop having a plurality of additional pinholes, each of said plurality of additional pinholes aligned with a corresponding one of said plurality of LEDs arranged in said circle, each of said plurality of additional pinholes passing only a portion of light from said corresponding one of said plurality of directional LEDs, wherein said portion of said light from said corresponding one of said plurality of LEDs arranged in said circle produces a directing light at a visually resolvable angle from said dot, said directing light appearing at a position that is between 135°–225° away from said angular orientation.

7. A biofeedback mechanism as in claim 6 wherein said directing light appears at said position as a dot of said directing light.

8. A biofeedback mechanism as in claim 6 wherein said plurality of LEDs arranged in said circle comprises at least four LEDs spaced equidistantly around said circle.

9. A biofeedback mechanism as in claim 1 wherein said second light source comprises:
   a light emitting diode (LED) for producing visible light;
   a field stop having a pinhole positioned in front of said LED for passing only a portion of said visible light as said dot; and
   a controller responsive to said eye movement error signal for controlling the production of said visible light by said LED.

10. A biofeedback mechanism as in claim 9 wherein said eye movement error signal includes angular orientation of said quantifiable amount of movement of said eye, said biofeedback mechanism further comprising:
   a third light source consisting of a plurality of LEDs arranged in a circle centered about said LED producing said visible light used for producing said dot; and
   said field stop being positioned in front of said plurality of LEDs arranged in said circle, said field stop having a plurality of additional pinholes, each of said plurality of additional pinholes aligned with a corresponding one of said plurality of LEDs arranged in said circle, each of said plurality of additional pinholes passing only a portion of light from said corresponding one of said plurality of directional LEDs, wherein said portion of said light from said corresponding one of said plurality of LEDs arranged in said circle produces a directing light at a visually resolvable angle from said dot, said directing light appearing at a position that is between 135°–225° away from said angular orientation.

11. A biofeedback mechanism as in claim 10 wherein said directing light appears at said position as a dot of said directing light.

12. A biofeedback mechanism as in claim 10 wherein said plurality of LEDs arranged in said circle comprises at least four LEDs spaced equidistantly around said circle.

13. A biofeedback mechanism as in claim 1 wherein said second light source continually produces said dot in one of at least two different colors and wherein said second light source changes color of said dot based on said eye movement error signal.

14. A biofeedback mechanism as in claim 1 wherein said eye movement error signal includes angular orientation of said quantifiable amount of movement of said eye, said biofeedback mechanism further comprising a third light source for producing a directing light at a visually resolvable angle from said dot, said directing light appearing at a position that is between 135°–225° away from said angular orientation.

15. A biofeedback mechanism as in claim 14 wherein said third light source includes means for controlling an "on"/"off" sequence of said directing light based on said angular orientation.

16. A method of biofeedback that provides eye position feedback to a patient, comprising the steps of:
   producing a ring of visible light centered about an optical axis and perceivable by an eye of said patient at a first position, said eye having a visual axis;
   producing a dot of visible light centered on said optical axis and perceivable by said eye of said patient at a second position, wherein said first position is perceived by said eye as being closer to said eye than said second position, and wherein said eye perceives said dot as being centered in said ring when said eye moves said visual axis into spatial and angular alignment with said optical axis;
   detecting a quantifiable amount of movement of said eye using an eye movement sensor; and
   altering visual appearance of said dot based on said quantifiable amount of movement of said eye to indicate to said patient to realign said visual axis with said optical axis of said dot and said ring.

17. A method according to claim 16 wherein said step of producing said ring comprises the steps of:
   providing a reticle having a circular channel cut in one face thereof nearest said eye, said circular channel centered on said optical axis and lying in a plane that is orthogonal to said optical axis; and
   illuminating said reticle from a position approximately 90° to said optical axis.

18. A method according to claim 17 wherein said circular channel has a v-shaped cross-section to reflect light in all directions diffusely.

19. A method according to claim 17 wherein said step of illuminating is accomplished using white light.

20. A method according to claim 16 further comprising the step of controlling an "on"/"off" sequence of said dot based on said quantifiable amount of movement.

21. A method according to claim 16 wherein said step of producing said dot comprises the step of continually producing said dot in one of at least two different colors and wherein said dot changes color based on said quantifiable amount of movement.

22. A method according to claim 16 wherein said quantifiable amount of movement includes angular orientation of said quantifiable amount of movement, said method further comprising the step of producing a directing light at a visually resolvable angle from said dot, said directing light appearing at a position that is between 135°–225° away from said angular orientation.

23. A method according to claim 22 wherein said step of producing said directing light includes the step of controlling an "on"/"off" sequence of said directing light based on said angular orientation.

* * * * *